United States Patent [19]
Eisele et al.

[11] Patent Number: 5,921,237
[45] Date of Patent: Jul. 13, 1999

[54] DRY POWDER INHALER

[75] Inventors: Robert F. Eisele; Karen Davies, both of San Diego, Calif.; Nelson Holton, Boulder, Colo.; Tim Kline, Boulder, Colo.; Ian Smith, Boulder, Colo.

[73] Assignee: Dura Pharmaceuticals, Inc., San Diego, Calif.

[21] Appl. No.: 08/681,103

[22] Filed: Jul. 22, 1996

Related U.S. Application Data

[63] Continuation-in-part of application No. 08/428,960, Apr. 24, 1995, Pat. No. 5,622,166.

[51] Int. Cl.⁶ .................................................. A61M 15/00
[52] U.S. Cl. ............................... 128/203.21; 128/203.15; 128/203.12
[58] Field of Search ........................ 128/203.15, 203.21, 128/203.12

[56] References Cited

U.S. PATENT DOCUMENTS

| | | |
|---|---|---|
| 4,307,734 | 12/1981 | Blankenship . |
| 4,627,432 | 12/1986 | Newell et al. . |
| 4,778,054 | 10/1988 | Newell et al. . |
| 4,811,731 | 3/1989 | Newell et al. . |
| 4,971,221 | 11/1990 | Urquhart et al. . |
| 5,033,463 | 7/1991 | Cocozza . |
| 5,035,237 | 7/1991 | Newell et al. . |
| 5,161,524 | 11/1992 | Evans . |
| 5,207,217 | 5/1993 | Cocozza et al. . |
| 5,327,883 | 7/1994 | Williams et al. . |
| 5,349,947 | 9/1994 | Newhouse et al. . |
| 5,469,843 | 11/1995 | Hodson . |
| 5,492,112 | 2/1996 | Mecikalski et al. ................ 128/203.15 |
| 5,622,166 | 4/1997 | Eisele et al. ........................ 128/203.21 |
| 5,645,051 | 7/1997 | Schultz et al. ...................... 128/203.15 |

FOREIGN PATENT DOCUMENTS

| | | |
|---|---|---|
| 0 129 985 A1 | 1/1985 | European Pat. Off. . |
| 0 211 595 A3 | 2/1987 | European Pat. Off. . |
| 2 142 246 | 1/1985 | United Kingdom . |
| 2 242 134 | 9/1991 | United Kingdom . |
| WO 91/06333 | 5/1991 | WIPO . |
| WO 94/08552 | 4/1994 | WIPO . |
| WO 94/20164 | 9/1994 | WIPO . |
| WO 95/11714 | 5/1995 | WIPO . |
| WO 96/09085 | 3/1996 | WIPO . |

OTHER PUBLICATIONS

Information Sheet—Example on Two Capsule Systems and the Diskhaler System, 4 pages.

*Primary Examiner*—Aaron J. Lewis
*Attorney, Agent, or Firm*—Lyon & Lyon LLP

[57] ABSTRACT

A drug powder inhaler has a cover plate pivotably attached to a lid on an inhaler housing. A lever is pivotably attached to the cover plate. A blister pack disk is rotatably mounted on the housing under the cover plate. A powder duct in the housing extends from a staging chamber underneath one end of the lever to an aerosolizing chamber. An actuator in the housing is pressed to shear open a blister on the blister pack disk and thereby deliver the drug dose contents of the blister into the staging chamber. A switch senses pressure in the mouthpiece and switches on a motor spinning an impeller within the aerosolizing chamber, when inhalation is detected.

19 Claims, 12 Drawing Sheets

DRY POWDER INHALER

This application is a continuation-in-part of Ser. No. 08/428,960, filed Apr. 24, 1995 and now U.S. Pat. No. 5,622,166, and incorporated herein by reference.

BACKGROUND OF THE INVENTION

FIELD OF THE INVENTION

The field of the invention is inhalers. More specifically, the invention relates to inhalers for delivering drugs in a solid finely divided dry powder or fluid form.

Inhalers are used to deliver drugs into a patient's lungs. Typically, an inhaler contains or provides a mixture of drugs and air or propellants. The mixture is delivered via the patient inhaling from a mouthpiece on the inhaler, for treatment of various conditions, for example, bronchial asthma. However, delivery of drugs via inhalation can be used for many other treatments, including those unrelated to lung condition.

One well known inhaler, the Diskhaler, described in U.S. Pat. No. 4,627,432, uses individual drug doses sealed within blisters on a blister disk. The disk is advanced by a knob with each successive dose. However, while the device described in U.S. Pat. No. 4,627,432 has met with varying degrees of success, disadvantages remain in indexing or advancing a blister disk within an inhaler, with opening the blisters to access the drug contents, with reliably providing intended dosages, and in other areas.

Accordingly, it is an object of the invention to provide an improved inhaler.

SUMMARY OF THE INVENTION

To these ends, the present inhaler preferably includes a cover plate pivotably attached to a lid on an inhaler housing. A blister pack disk is rotatably mounted on the housing under the cover plate, and is movable in a single forward direction. An actuator in the housing is most desirably aligned with a lever on the cover plate. The patient pushes the actuator which shears open a blister on the disk and then causes the lever to crush the blister, to deliver the drug powder contents of the blister into a duct within the housing, for subsequent inhalation by the patient.

Other and further objects will appear hereinafter.

BRIEF DESCRIPTION OF THE DRAWINGS

In the drawings, wherein similar reference characters denote similar elements throughout the several views.

DETAILED DESCRIPTION OF THE PREFERRED EMBODIMENTS

Figure 1:
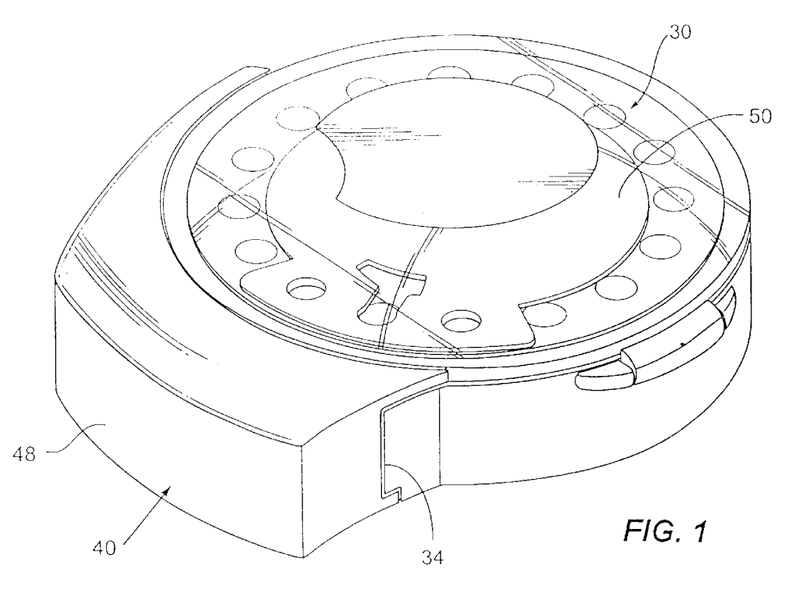
FIG. 1 is perspective view of the present inhaler with the mouthpiece covered by the cover assembly.
Figure 2:
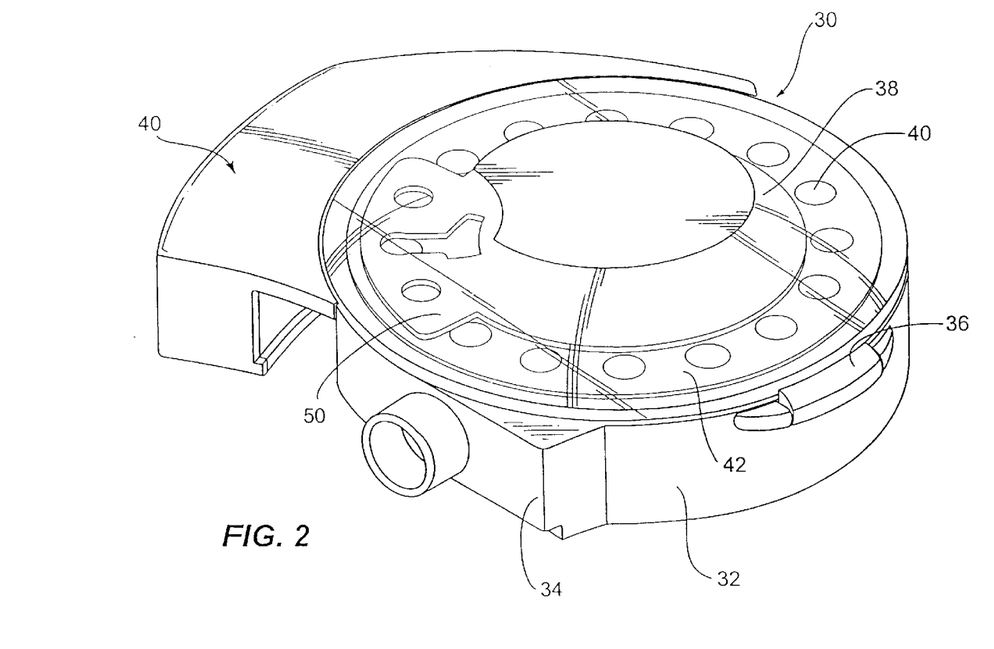
FIG. 2 is a perspective view thereof with the mouthpiece uncovered.
Figure 3:
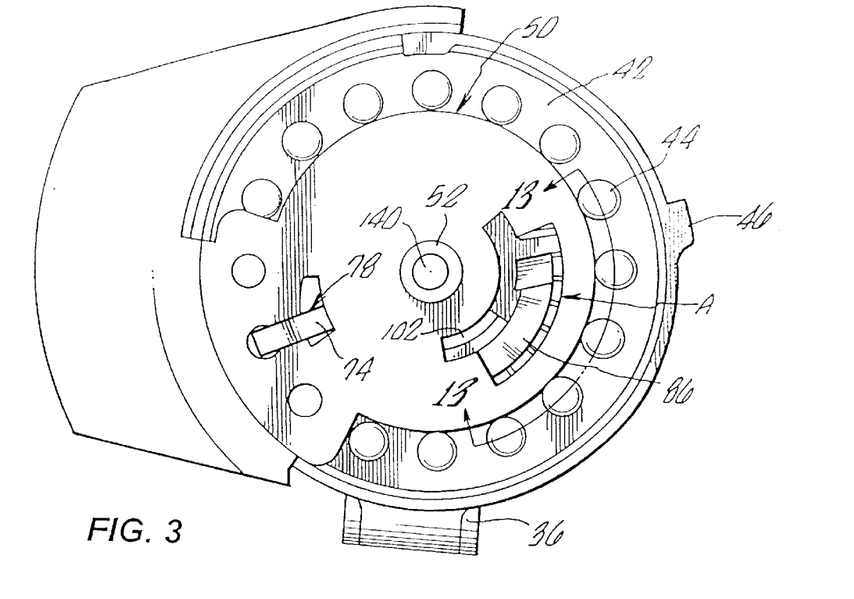
FIG. 3 is a plan view of the inhaler as shown in FIG. 1.
Figure 4:
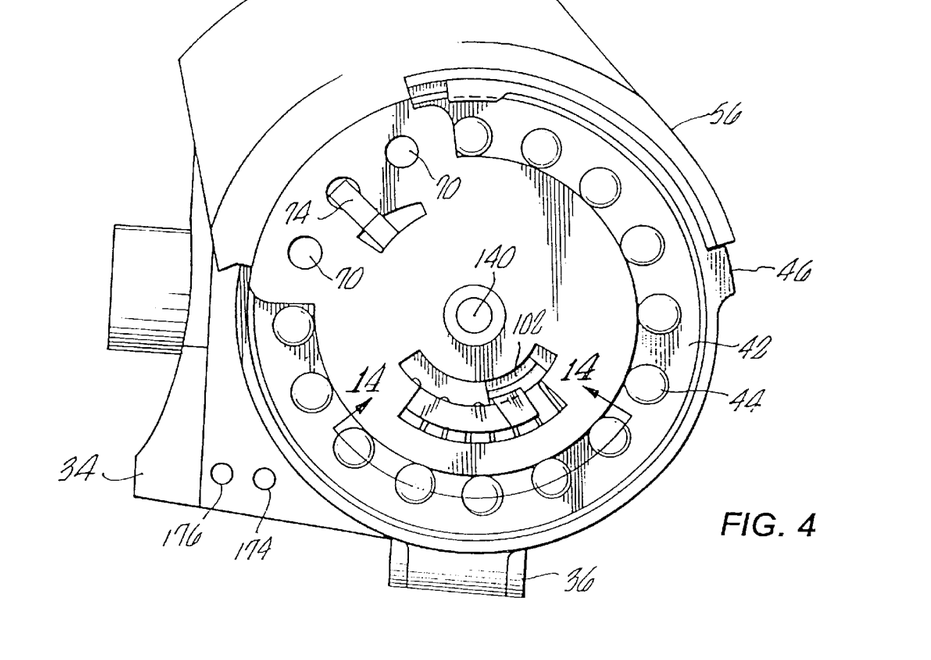
FIG. 4 is a plan view of the inhaler as shown in FIG. 2.

Turning now in detail to the drawings, as shown in FIGS. 1–4, a dry powder inhaler includes a housing 32 having a lid 38 attached to the housing with a hinge 36. The lid 38 is preferably a transparent material, e.g., clear plastic. A removable mouthpiece 34 is provided on one side of the housing 32. A sliding cover assembly 40 may be pivoted on the lid 38 from a closed position covering the mouthpiece 34, as shown in FIGS. 1 and 3, to an opened position exposing the mouthpiece 34, as shown in FIGS. 2 and 4. As best shown in FIGS. 3 and 4 (looking down through the transparent lid 38), a disk 42 having a plurality of radially spaced apart blisters 44 is generally centered on top of the housing 32 on a center post 140 extending upwardly from the housing 32. A lid stop 46 on the housing 32 limits sliding movement of the cover assembly 40 in the opened position.

Figure 8:
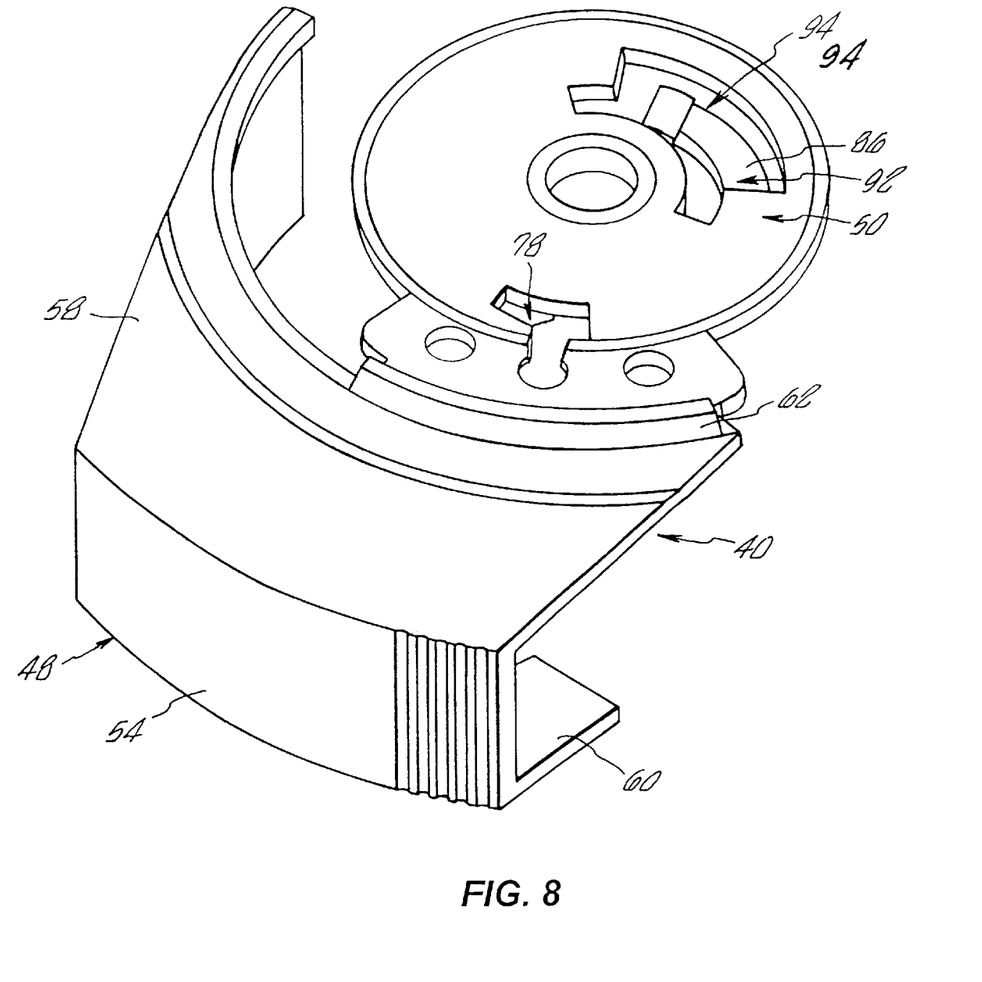
FIG. 8 is an enlarged top and front perspective view of the cover assembly on the inhalers of FIGS. 1 and 2.
Figure 9:
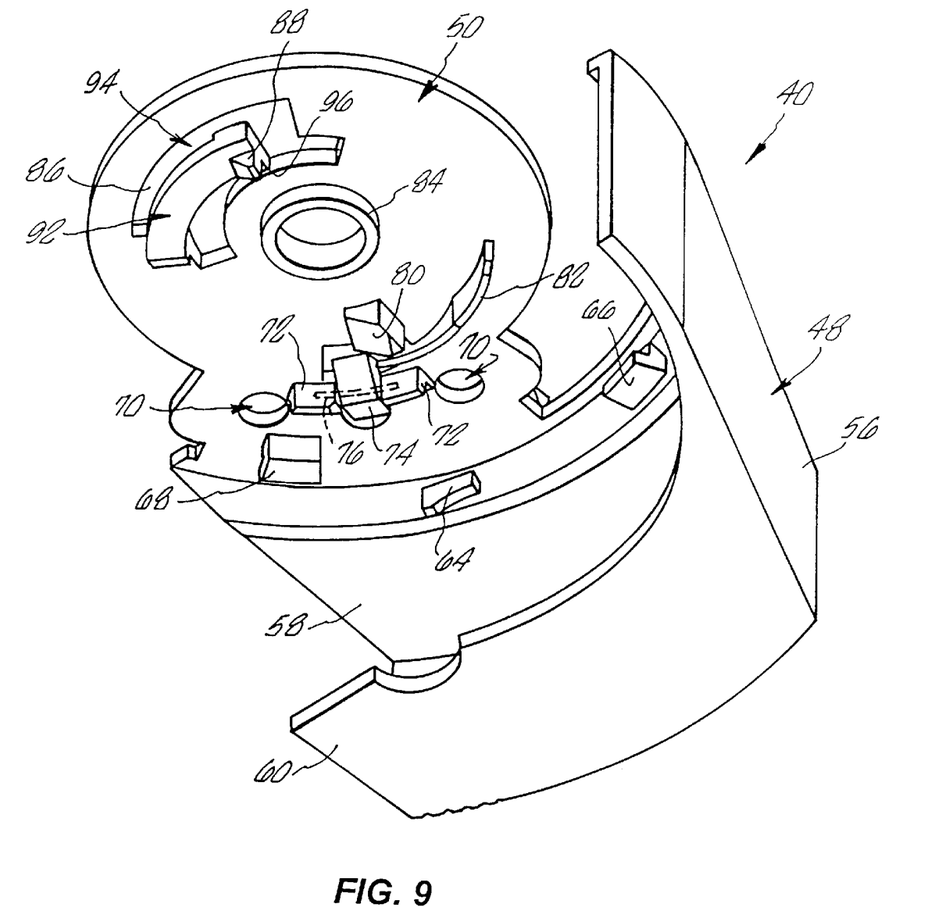
FIG. 9 is a bottom and rear perspective view of the cover assembly of FIG. 8.
Figure 18:
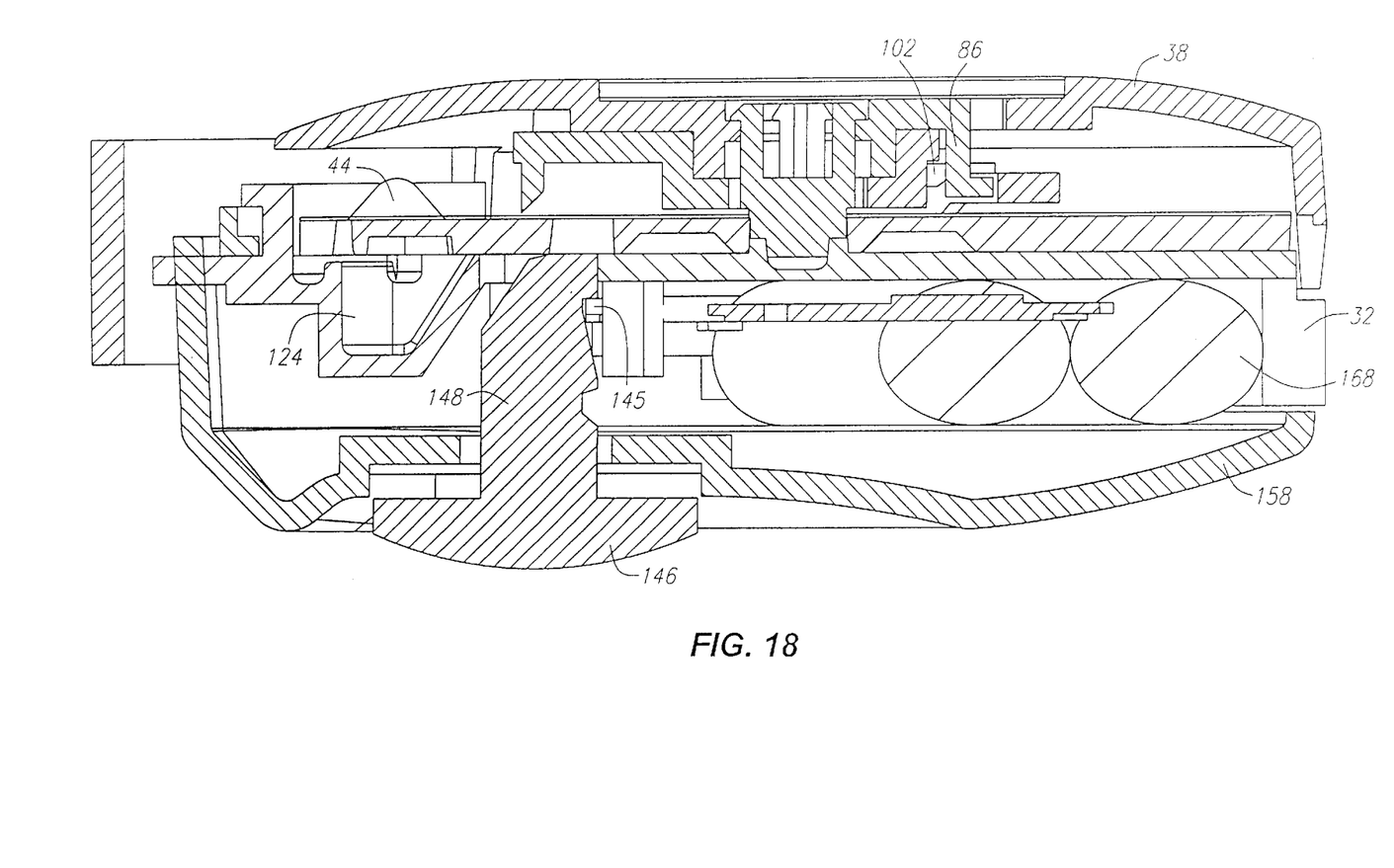
FIG. 18 is a section view taken along line 18—18 of FIG. 5.

Turning momentarily to FIGS. 8 and 9, the sliding cover assembly 40 includes an enclosure 48 having a front curved wall 54, a side wall 56, a top wall 58 and a bottom wall 60. A rim 62 extends upwardly and radially inwardly on the top wall 58. Referring now to FIG. 9, a glide block 64 and an outside retainer 66 extend downwardly and inwardly on the underside of the top wall 58. A generally flat cover plate 50 is preferably integrally formed with the enclosure 48, with the cover plate 50 and enclosure comprising the cover assembly 40. An inside retainer 68 on the cover plate 50 extends radially outwardly. A lever 74 is pivotably supported on a lever pin 76 held in place by lever blocks 72 on the underside of the cover plate 50. The lever 74 can pivot through a lever opening 78 in the cover plate 50, as best shown in FIG. 8. A ramp 80 and a guide wall 82 project downwardly from the cover plate 50, adjacent to the lever 74, as shown in FIG. 9. The entire cover assembly 40, which includes the enclosure 48 and cover plate 50 is pivotably attached to the lid 38, with the lid post 52 extending through a center hub 84 on the cover plate 50. Clearance holes 70 through the cover plate 50 on either side of the lever opening 78 allow the cover plate to sit on top of the blister disk, as shown in FIG. 18, without excessive vertical interference.

Figure 10:
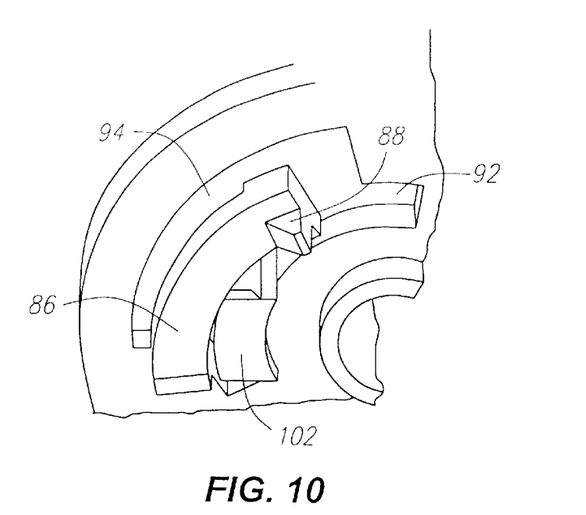
FIG. 10 is an enlarged view of features shown in FIG. 9.
Figure 13:
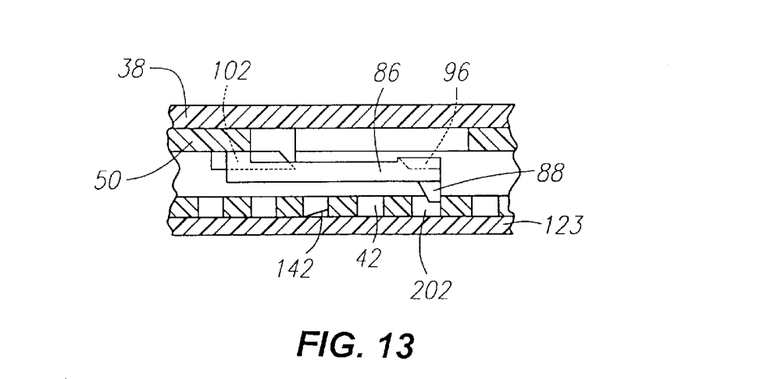
FIG. 13 is a partial section view taken along line 13—13 of FIG. 3.
Figure 14:
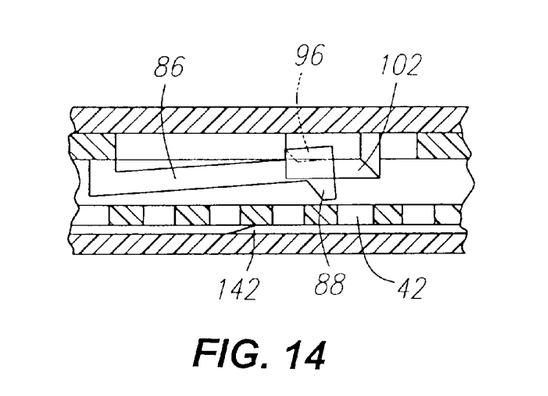
FIG. 14 is a partial section view taken along line 14—14 of FIG. 4.

Referring to FIGS. 8, 9 and 10, a spring arm 86 having a downwardly projecting end tab 88 is attached to or integral with the cover plate 50. As shown in FIG. 13, the spring arm 86 includes an arm wedge 96 at its free end, alongside the tab 88. As shown in FIG. 10, an arm lifter 102 extends downwardly from the lid 38. An outer slot 94 through the cover plate 50 overlies the spring arm 86. An inner slot 92 adjoining the outer slot 94 through the cover plate 50 provides clearance for the arm lifter 102, and allows the cover assembly 40 to rotate (preferably about 90°). The arm lifter 102 includes an internal ramp, and is dimensioned to engage the arm wedge 96, and lift the arm 86 up towards the lid 38, as the arm wedge 96 moves into full engagement with the lifter 102.

Figure 5:
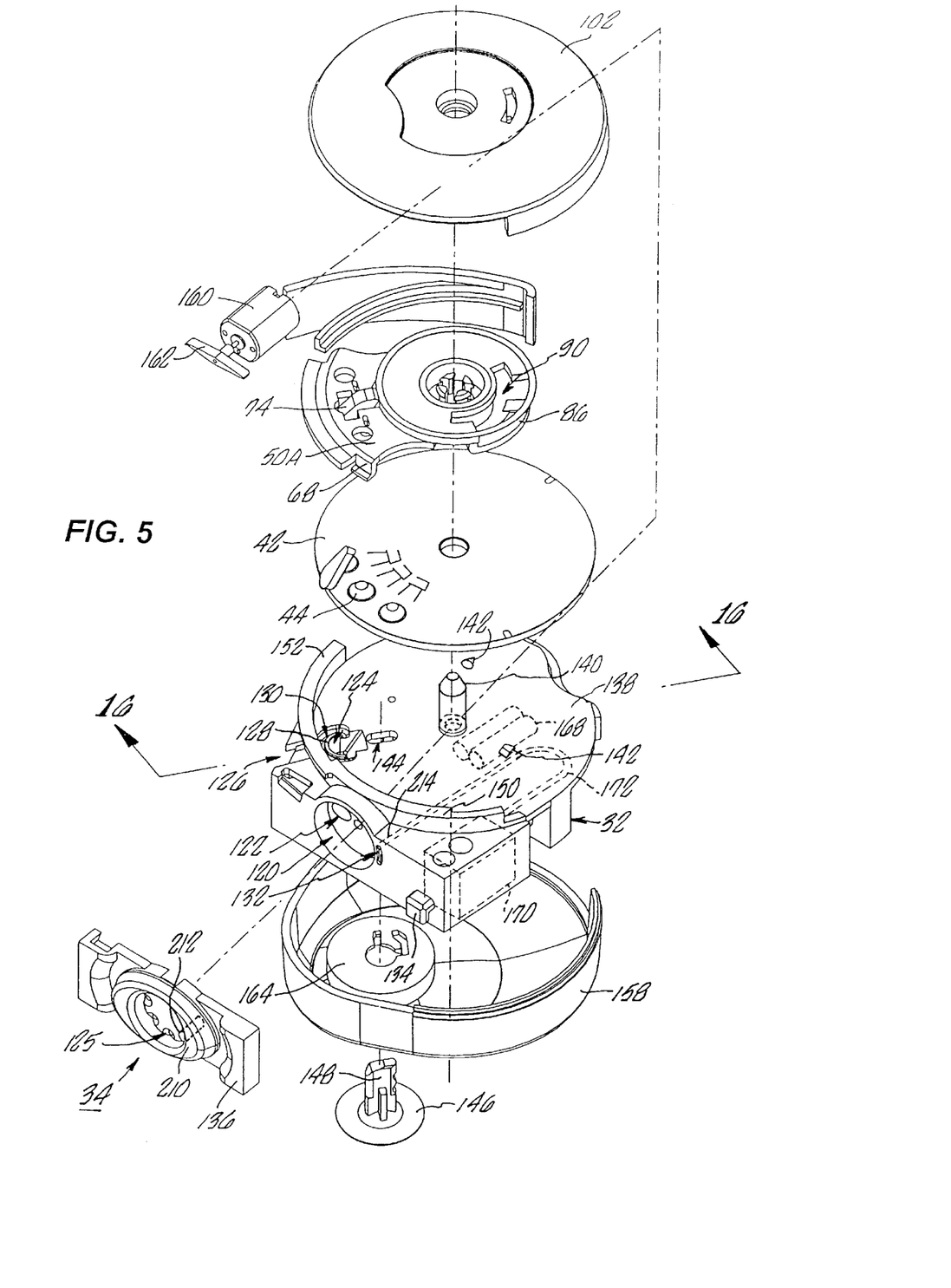
FIG. 5 is an exploded perspective view of the inhaler of FIGS. 1 and 2.
Figure 6:
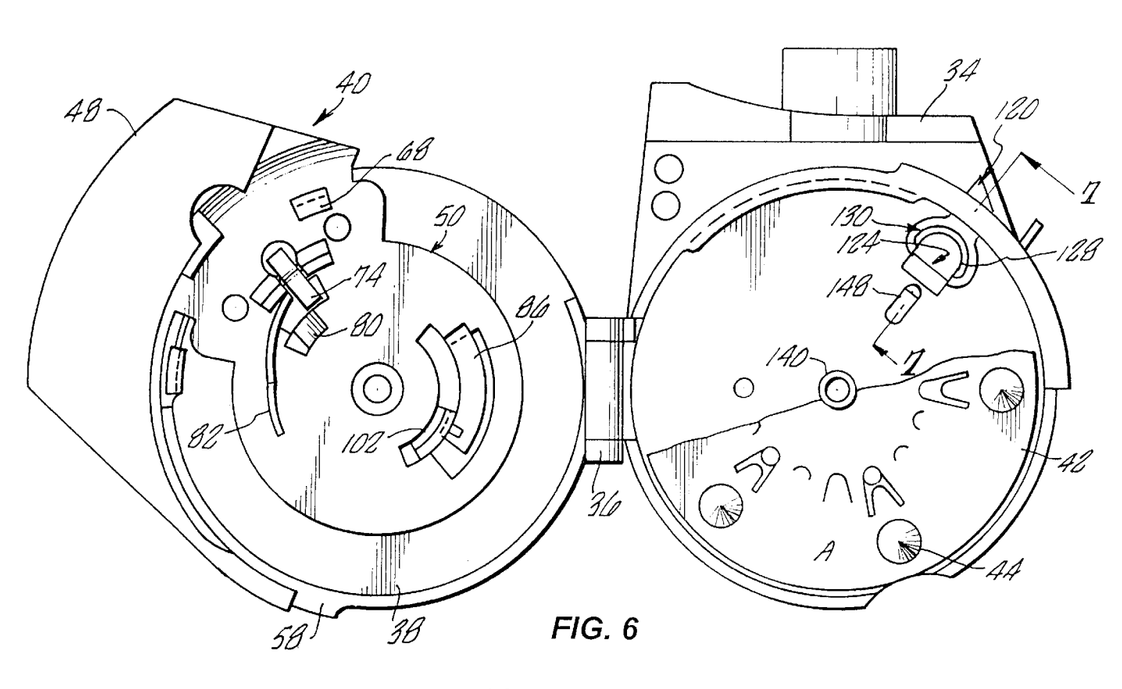
FIG. 6 is an plan view of the inhaler of FIGS. 1 and 2 with the lid open.
Figure 7:
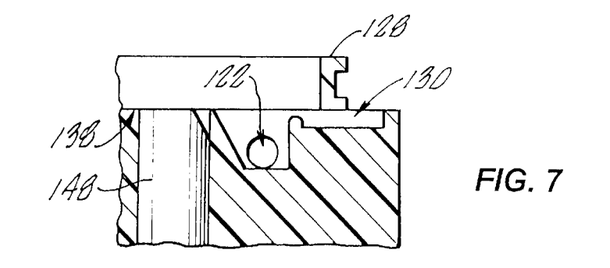
FIG. 7 is a partial section view taken along line 7—7 of FIG. 6.

Turning now to FIG. 5, the housing 32 includes a mixing chamber 120, and a staging chamber 124 connected to the mixing chamber 120 via a duct 122. Referring now also to FIGS. 6 and 7, an inlet duct 126 extends from one side of the housing 32 to the staging chamber 124 via a duct recess 130. A crescent barrier 128 around the top of the staging chamber 124 creates an indirect air flow path from outside of the housing, through the inlet duct 126 and into the staging chamber 124.

In a first embodiment of the present invention, referring once again to FIG. 5, a pressure port or opening 132 in the housing 32 alongside the mixing chamber 120 connects to a pressure switch 170 via a tube 172. The pressure port aligns with a mouthpiece port 135 leading into the central opening of the mouthpiece. This provides a continuous duct from the mouthpiece opening to the pressure switch. The mouthpiece 34 or an alternative embodiment mouthpiece 136 is secured to the housing 32 with a hook 134. The mouthpiece is removable by twisting or rotating the mouthpiece, to disengage the hook 134, and then by pulling it off. Ratchet posts 142 having angled top surfaces project slightly above the flat top surface 138 of the housing 32. An actuation button 146 has a post 148 extending entirely through a post opening 144 in the housing 32.

Referring momentarily to FIG. 18, a detent 145 on the housing engages and holds the post 148 in the up position (driving the lever to crush a blister), until the disk is advanced to the next blister. At the front of the housing, behind the mixing chamber 120, is an inwardly projecting housing inner rim 150, and an outwardly projecting housing outer rim 152. The outer rim 152 is engaged by the outside retainer 66, and the inner rim is engaged by the inside retainer 68, as the cover assembly 40 is moved between opened and closed positions. The interaction of the inner rim 150 and inside retainer 68 and outer rim 152 and outside retainer 66, holds the cover assembly and lid down on top of the housing 32.

Referring still to FIG. 5, a bottom cover 158 attached to the housing 32 has a button recess 164 around the actuation button 146, so that the actuation button 146 does not project beyond the bottom surface of the cover 158. An impeller 162 within the mixing chamber 120 is supported on the shaft of an electric motor 160 behind the mixing chamber 120 in the housing 32. The motor 160 is wired to batteries 168 and the pressure switch 170. A battery indicator LED 174 and a status indicator LED 176 are positioned in the housing 32, above the pressure switch 170.

Figure 20:
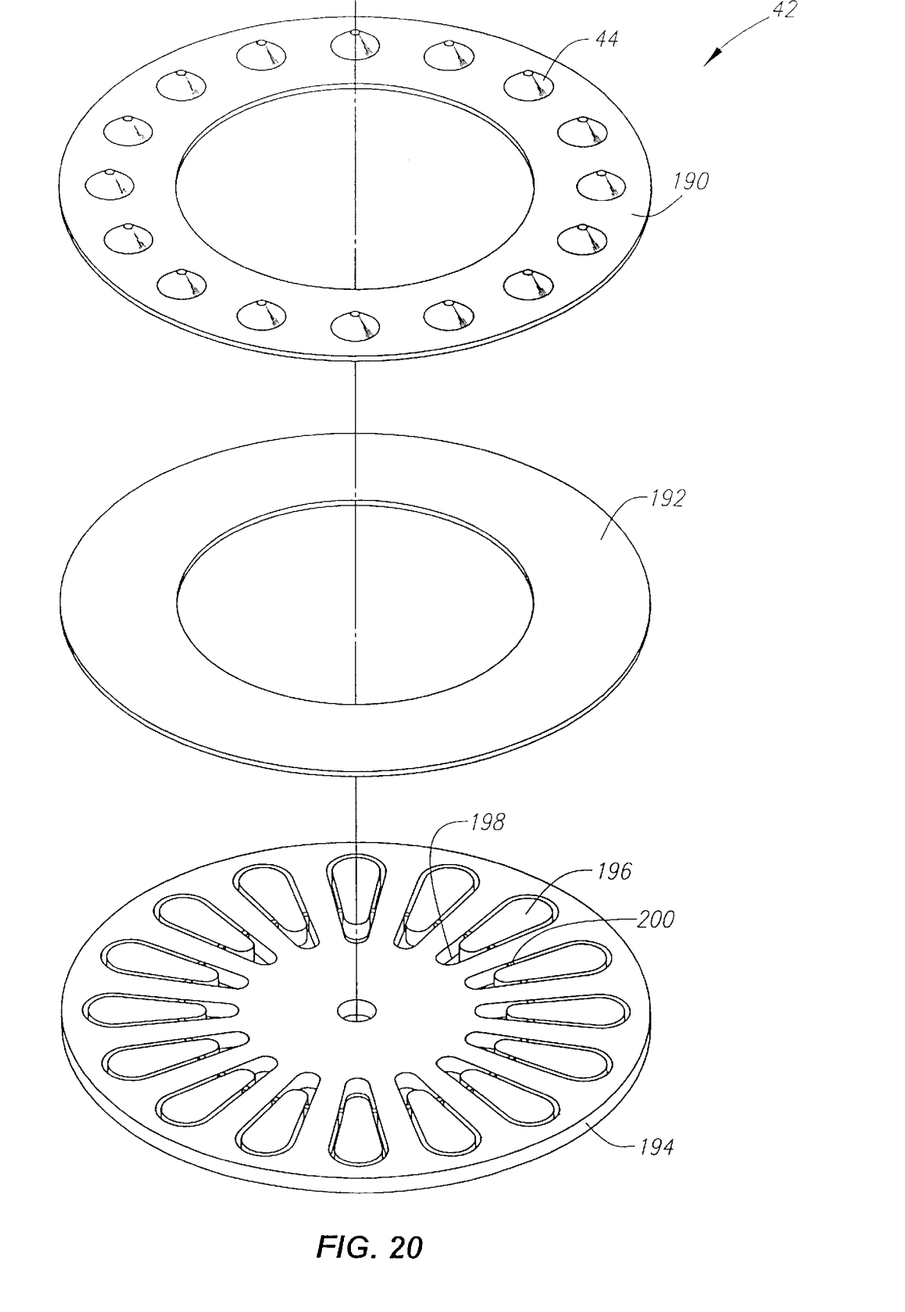
FIG. 20 is an exploded perspective view of a blister disk for use with the inhaler shown in FIGS. 1 and 2.
Figure 21:
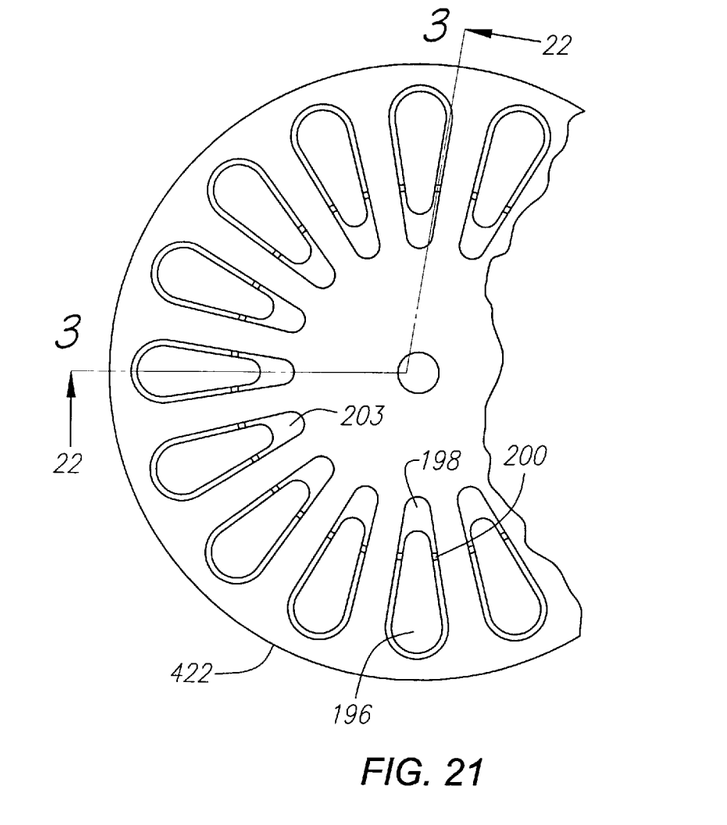
FIG. 21 is a partial plan view thereof.
Figure 22:
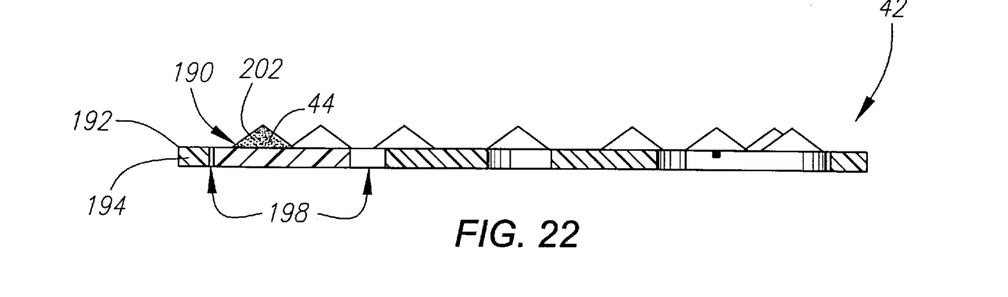
FIG. 22 is a section view taken along line 22—22 of FIG. 21.

Turning now to FIGS. 20–22, the disk 42 includes a blister foil ring 190, preferably a metal or aluminum foil having generally conical blisters formed in it. The blister foil ring 190 and a foil seal ring 192 are adhered or bonded onto a carrier disk 194. As shown in FIG. 21, the carrier disk 194 has tabs 196 suspended within tab slots 198 by bridges 200. Each blister 44 on the blister foil ring 190 is aligned over a tab 196. The bridges 200 hold the tabs 196 in position, but allow the tab to pivot about the bridges, with nominal torque. As shown in FIG. 22, powdered drug 202 is sealed within the blisters 44. The carrier disk 194 is preferably plastic. The tab supports 200 are small enough to support the tabs 196, but also to allow the tab to pivot under force of the post of the actuation button.

In use, a disk 42 is first loaded into the inhaler 30 by sliding the cover assembly 40 from the closed position shown in FIG. 1 to the open position shown in FIG. 2. In this position, the lid 38 and cover assembly 40 are still held down on top of the housing 32 by the interaction of the outside retainer 66 and inside retainer 68 on the housing outer rim 152 and inner rim 150. The side wall 56 of the enclosure 48 is lifted slightly away from the housing 32, to a allow it to pass over the lid stop 46. As this occurs, the retainers 66 and 68 move off of and release from the inner and outer rims 150 and 152. The cover assembly 40 and lid 38 are then pivoted upwardly about the hinge 36, to open up the inhaler 30, as shown in FIG. 6, for placement or replacement of a disk 42.

A disk 42 is placed over the center post 140 over the housing top surface 138 with the blisters 44 on top. The lid 38 and cover assembly 40 are pivoted back about the hinge 36, from the position shown in FIG. 6, to the position shown in FIG. 2. The inhaler 30 is then ready for use.

The rachet posts 142 on the housing top surface 138 project slightly into the open ends 203 of the tab slots 198. The disk 42 is accordingly oriented so that a blister 44 will be aligned over the staging chamber 124. The rachet posts 142 also prevent the disk 42 from moving in reverse (i.e., clockwise in FIG. 6).

With the lid 38 closed, but with the cover assembly 40 opened (as shown in FIG. 2), the inner end of the lever 74 is aligned over the top of the post 148. The outer end of the lever 74 is aligned over the top of a blister 44, and over the staging chamber 124.

Figure 11:
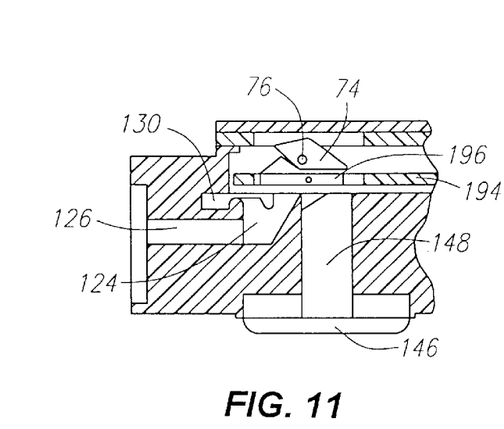
FIG. 11 is a partial section view taken along line 11—11 of FIG. 5.
Figure 12:
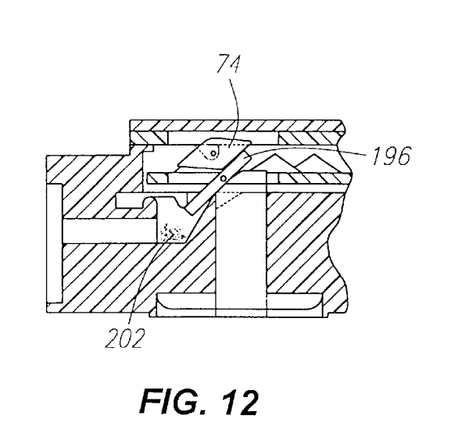
FIG. 12 is similar view showing positions of various components during use of the device.
Figure 19:
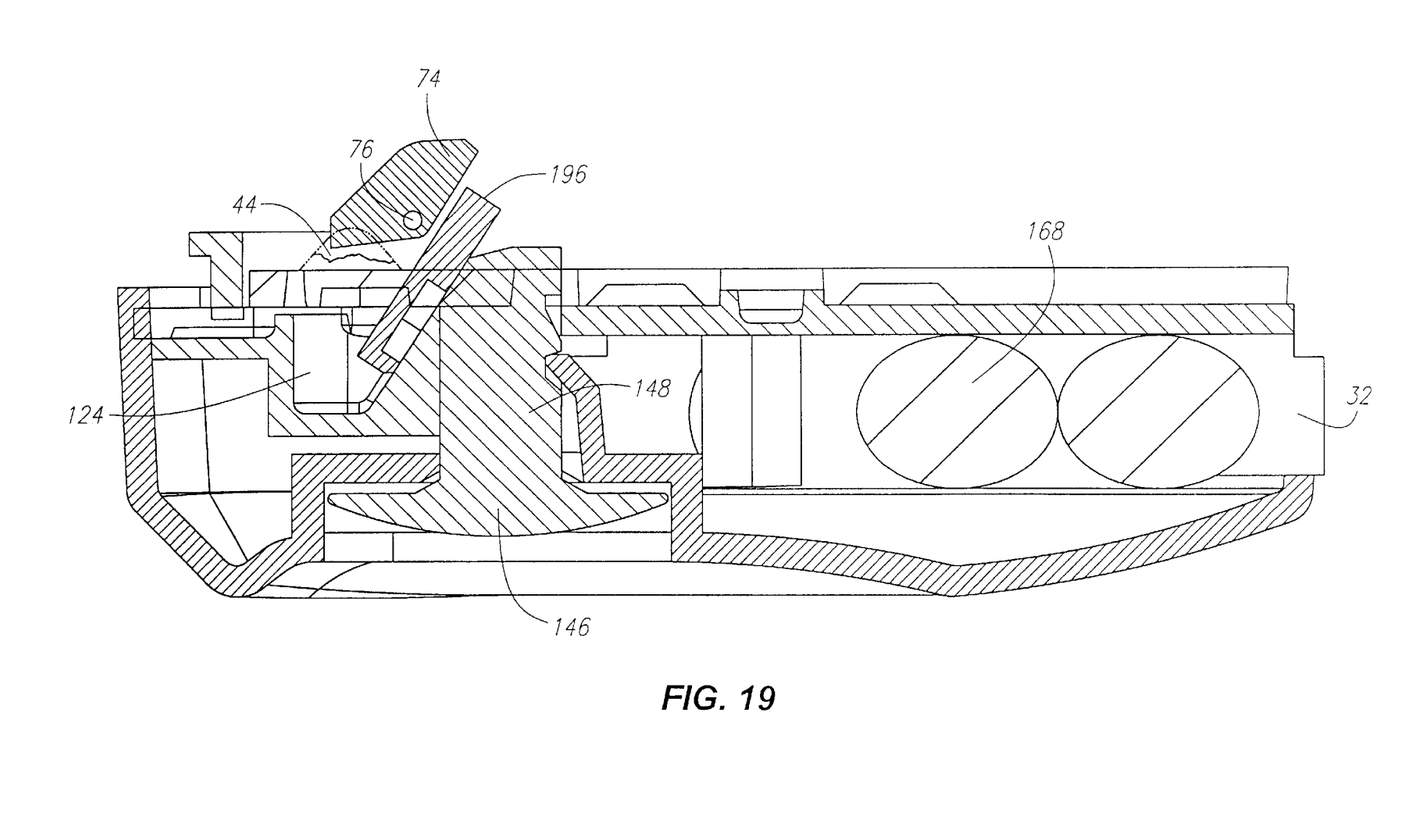
FIG. 19 is a similar view thereof with various components omitted for drawing clarity, and showing positions of components during use.

With the inhaler 30 preferably held upright, the actuation button 146 is pushed up. As shown in FIGS. 11, 12 and 19, the upward movement of the post 148 on the actuation button 146 first pivots the tab 196 on the blister 44 over the staging chamber 124. The tab pivots on the bridges 200. As this occurs, the foil seal ring 192 sealing the blister 44 on the bottom shears away opening the blister and allowing the powdered drug 202 to fall into the staging chamber 124.

As upward movement of the post 148 continues, the post pivots the lever 74 causing the outer end of the lever to crush the blister 44 down, to release any residual powder into the staging chamber 124.

With one dose of the powdered drug now delivered from a sealed blister 44 into the staging chamber 124, the patient places the mouthpiece 34 into the mouth and inhales. The inhalation draws air from outside of the housing through the inlet duct 126, around and under the crescent barrier 128 and into the staging chamber 124. Air and powdered drug 202 move through the duct 122 and into the mixing chamber 120. At the same time, upon inhalation, the reduced air pressure at the mouthpiece 136 is detected by the pressure switch 170 via the tube 172 extending to the pressure port 132. The switch 170 turns on the motor 160, spinning the impeller 162 within the mixing chamber 120. The spinning impeller tends to further draw in air and powdered drug through the duct 122 into the mixing chamber 120. The air and drug is mixed in the mixing chamber 120, as further described in U.S. Pat. No. 5,327,883, and U.S. Pat. No. 5,577,497, incorporated herein by reference. As the impeller is already spinning at high speed when the drug enters the mixing chamber, the air/drug mixing and deagglomeration are enhanced.

The patient inhales on the mouthpiece drawing in the air/drug mixture from the mixing chamber 120 via holes 125 in the rear wall of the mouthpiece 34 (which rear wall also forms the front wall of the mixing chamber 120).

To prepare for delivery of the next dose, the cover assembly 40 is moved from the position shown in FIG. 2, to the position shown in FIG. 1, to cover the mouthpiece 34. As this closing movement of the cover assembly 40 occurs, the arm wedge 96 on the spring arm 86 is released from the lifter 102. This allows the spring arm 86 to flex downwardly with the tab 88 engaging into the opened end 203 of a tab slot 198, approximately at position A as shown in FIGS. 3 and 6. With the continued closing motion of the cover assembly 40 to the position shown in FIG. 3, the tab 88 on the spring arm 86 advances the disk 42 to the next blister 44 (moving the disk 42 counter-clockwise in FIG. 3). For a disk having 16 blisters, the advancing movement, from engagement of the tab 88 to the disk 42, until the end of movement, is about 22°. As the disk 42 is advanced by the spring arm 86 on the closing cover assembly 40, the disk 42 rides up and over the angled top surfaces of the rachet posts 142 and then settles back down onto the housing surface 138 with the rachet posts 142 engaged into the next set of opened ends 203 of the tab slots 198. In this manner, the next blister 44 on the disk 42 is positioned for delivery and inhalation, as described above. When the cover assembly 40 is reopened, to the position shown in FIG. 4, the disk 42 does not move, as the spring arm 86 is lifted up and out from engagement with the disk by the interaction of the lifter 102 on the lid 38 and the arm wedge 96 on the spring arm 86. Through this repeated motion of opening and closing the cover assembly 40, each blister 44 on the disk 42 can be sequentially accessed, until all of the blisters are used.

Figure 15:
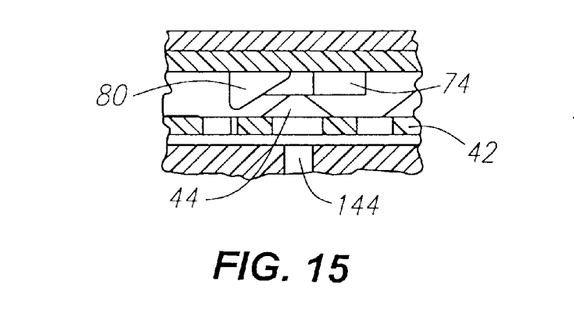
FIGS. 15, 16 and 17 are partial section view fragments illustrating movement of components within the device.
Figure 16:
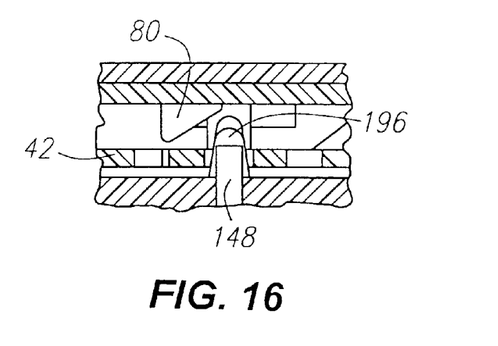
Figure 17:
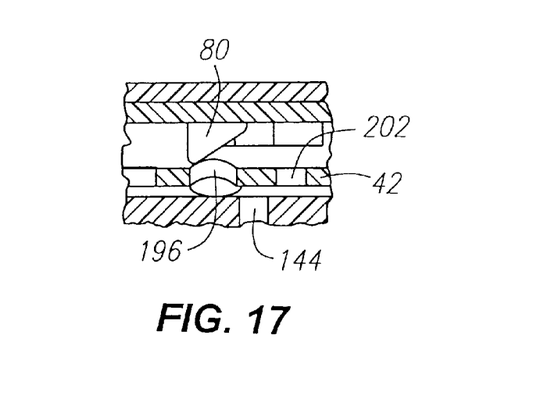

As the cover assembly 40 is closed, the ramp 80 on the cover plate 50 rides over the top of the post 148, the push it down, resetting the actuation button 146 for the next dose, as shown in FIGS. 15–17. Simultaneously, the guide wall 82, which ramps upwardly from the lever 74, pushes down on the pivoted tab 196 from the blister delivered. The tab 196 is accordingly pushed back down into the plane of the disk 42, so that the disk can be advanced without interference. The rachet posts 142 prevent the disk 42 from moving in reverse (clockwise in FIG. 3) at anytime.

Accordingly, a novel inhaler is described and shown with various advantages over the prior art design. The above-described inhaler may contain various changes and modifications, including various substitutions and equivalents, without departing from the spirit and scope of the present invention.

We claim:

1. An inhaler comprising:
   a housing;
   a cover plate pivotably attached to a lid on the housing;
   a lever pivotably attached to the cover plate, the lever having an actuator end and a blister end;
   a blister pack disk rotatably mounted on the housing, under the cover plate;
   a powder duct in the housing under the blister end of the lever; and
   an actuator extending through the housing and aligned with the actuator end of the lever.

2. The inhaler of claim 1 further comprising an enclosure attached to the cover plate.

3. The inhaler of claim 2 wherein the enclosure is pivotable with the cover plate on the housing from a first position wherein the enclosure covers the mouthpiece, to a second position wherein the mouthpiece is exposed.

4. The inhaler of claim 3 further comprising means for incrementally advancing the blister pack disk in one direction, with movement of the enclosure from the second position to the first position.

5. The inhaler of claim 2 further comprising an inside retainer and an outside retainer on the enclosure and slidably engageable to the housing.

6. The inhaler of claim 1 further comprising a removable mouthpiece on the housing.

7. The inhaler of claim 1 further comprising a ramp on the cover radially aligned with the actuator.

8. The inhaler of claim 7 further comprising a guidewall adjacent to the ramp.

9. The inhaler of claim 1 further comprising a hinge joint attaching the lid to the housing.

10. The inhaler of claim 1 further comprising a spring arm on the cover plate slidably engaged to a lifter on the lid.

11. The inhaler of claim 10 further comprising a tab at a free end of the spring arm adapted to engage a tab slot in the blister pack disk.

12. The inhaler of claim 1 further comprising racket posts on the housing underneath the blister pack disk.

13. The inhaler of claim 1 wherein the housing has a bottom and the actuator comprises a button on the bottom of the housing and post attached to the button and extending through the housing.

14. The inhaler of claim 13 further comprising a detent on the actuator.

15. The inhaler of claim 1 wherein the lid is transparent.

16. A method of powder inhalation by a patient comprising the steps of:
   placing a disk having blisters containing a powder on an inhaler;
   opening a blister and releasing powder from the blister into a staging chamber in the inhaler;
   sensing inhalation by the patient;
   spinning up an impeller in a mixing chamber in the inhaler in response to the sensed inhalation; and
   drawing air and the powder from the staging chamber into the mixing chamber, after the impeller is already spinning.

17. The method of claim 16 further comprising the step of pivoting a lever to crush the blister.

18. A method of delivering a powder medicament for inhalation by a patient comprising the steps of:
   providing a dry powder inhaler,
   providing a plurality of blisters on a carrier on the dry powder inhaler;
   pivoting a tab under the blister from a first tab position to a second tab position to shear the blister open;
   pivoting a lever on the inhaler from a first lever position to a second lever position, to crush the blister;
   moving the tab back to the first position; and
   advancing the carrier to open a subsequent blister.

19. A dry powder inhaler comprising:
   a housing having a top surface;
   at least one rachet post on the top surface;
   a cover attached to the housing;
   an arm pivotably attached to the housing, the arm having a fixed end and a free end;
   a tab extending from the free end of the arm toward the top surface of the housing; and
   a lifter on the cover, for raising and lowering the free end of the arm as the arm pivots about the housing.

* * * * *